United States Patent
Fay et al.

(10) Patent No.: US 8,138,773 B2
(45) Date of Patent: Mar. 20, 2012

(54) HYBRID RESILIENT AND FRANGIBLE LAYERED STRUCTURAL HEALTH SENSOR

(75) Inventors: Matthew K. Fay, Wentzville, MO (US); Greg L. Sheffield, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 580 days.

(21) Appl. No.: 12/202,883

(22) Filed: Sep. 2, 2008

(65) Prior Publication Data

US 2010/0052704 A1    Mar. 4, 2010

(51) Int. Cl.
*G01R 27/08* (2006.01)
(52) U.S. Cl. ....................................... 324/700
(58) Field of Classification Search ............ 324/700
See application file for complete search history.

(56) References Cited

U.S. PATENT DOCUMENTS

| | | | |
|---|---|---|---|
| 3,599,090 A * | 8/1971 | Fitzpatrick et al. | 324/508 |
| 4,087,800 A | 5/1978 | Lee | |
| 4,587,517 A | 5/1986 | Engstrom et al. | |
| 5,338,908 A * | 8/1994 | Rahman et al. | 200/83 P |
| 5,936,525 A | 8/1999 | Leyden et al. | |
| 5,952,836 A * | 9/1999 | Haake | 324/718 |
| 6,501,286 B1 * | 12/2002 | Balfanz et al. | 324/700 |
| 7,132,943 B2 | 11/2006 | Nelson | |
| 7,231,826 B2 | 6/2007 | Bossi et al. | |
| 7,239,156 B1 * | 7/2007 | Hladky et al. | 324/700 |
| 7,333,898 B2 | 2/2008 | Griess et al. | |
| 7,388,166 B2 | 6/2008 | Marmaropoulos et al. | |
| 7,434,480 B2 | 10/2008 | Georgeson et al. | |
| 7,621,193 B2 * | 11/2009 | Fay et al. | 73/865.9 |
| 2002/0145529 A1 | 10/2002 | Kuzik et al. | |
| 2003/0164700 A1 * | 9/2003 | Goldfine et al. | 324/235 |
| 2006/0144997 A1 | 7/2006 | Schmidt et al. | |
| 2007/0125189 A1 | 6/2007 | Bossi et al. | |
| 2007/0144272 A1 | 6/2007 | Yu et al. | |
| 2007/0252718 A1 | 11/2007 | Ray | |
| 2008/0109187 A1 | 5/2008 | Kollgaard et al. | |
| 2008/0163670 A1 | 7/2008 | Georgeson | |
| 2008/0167833 A1 | 7/2008 | Matsen et al. | |
| 2008/0223152 A1 | 9/2008 | Georgeson et al. | |

OTHER PUBLICATIONS

Greene, "Sensors Without Batteries," http://www.technologyreview.com/read_article.aspx?id=16864&ch=infotech&a=f, Technology Review Published by MIT, May 15, 2006.
Eckfeldt, "What Does RFID Do for the Consumer?," Comm. of the ACM, Sep. 2005, vol. 48, No. 9, pp. 77-79.

(Continued)

*Primary Examiner* — Jeff Natalini
(74) *Attorney, Agent, or Firm* — Canady & Lortz LLP; Bradley K. Lortz

(57) ABSTRACT

A sensor for monitoring and testing for both possible fractures and corrosion in structural elements is disclosed. A frangible material layer including a thin breakable conductor sense loop and a resilient material layer including a conductive corrosion sense loop bonded on top of the frangible layer form an assembly which is bonded to a structural element to be tested. Portions of the conductive corrosion sense loop are exposed through weep holes in the resilient material layer. A fracture in the bonded structural element induces a disruption in both the frangible membrane and the thin breakable conductor sense loop and corrosion of the conductive corrosion sense loop changes its electrical properties. Measured electrical property changes of the disrupted conductor sense loop and/or the conductive corrosion sense loop reveal possible damage. Both sensor layers may utilize a single shared wireless communications tag to couple to an electrical measuring device.

20 Claims, 7 Drawing Sheets

OTHER PUBLICATIONS

Gunther et al., "RFID and the Perception of Control: The Consumer's View," Comm. of the ACM, Sep. 2005, vol. 48, No. 9, pp. 73-76.

Ohkubo et al., "RFID Privacy Issues and Technical Challenges," Comm. of the ACM, Sep. 2005, vol. 48, No. 9, pp. 66-71.

Hsi et al., "RFID Enhances Visitors' Museum Experience at the Exploratorium," Sep. 2005, vol. 48, No. 9, pp. 60-65.

Pering et al., "Spontaneous Marriages of Mobile Devices and Interactive Spaces," Sep. 2005, vol. 48, No. 9, pp. 53-59.

Sample et al., "Design of an RFID-Based Battery-Free Programmable Sensing Platform," IEEE Trans. on Instr. and Meas., vol. 57, No. 11, Nov. 2008, pp. 2608-2615.

Raskar et al., "Photosensing Wireless Tags for Geometric Procedures," Sep. 2005, vol. 48, No. 9, pp. 46-51.

Smith et al., "RFID-Based Techniques for Human-Activity Detection," Sep. 2005, vol. 48, No. 9, pp. 39-44.

Borriello, "RFID: Tagging the World," Sep. 2005, vol. 48, No. 9, pp. 34-37.

* cited by examiner

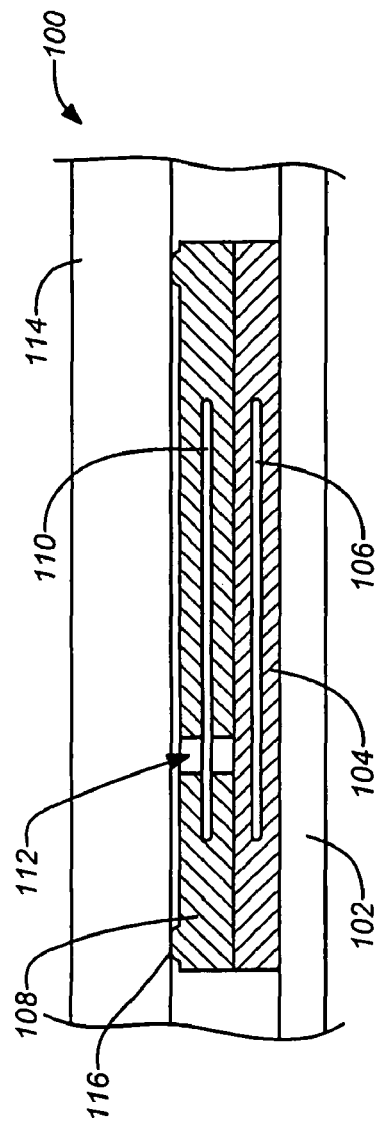
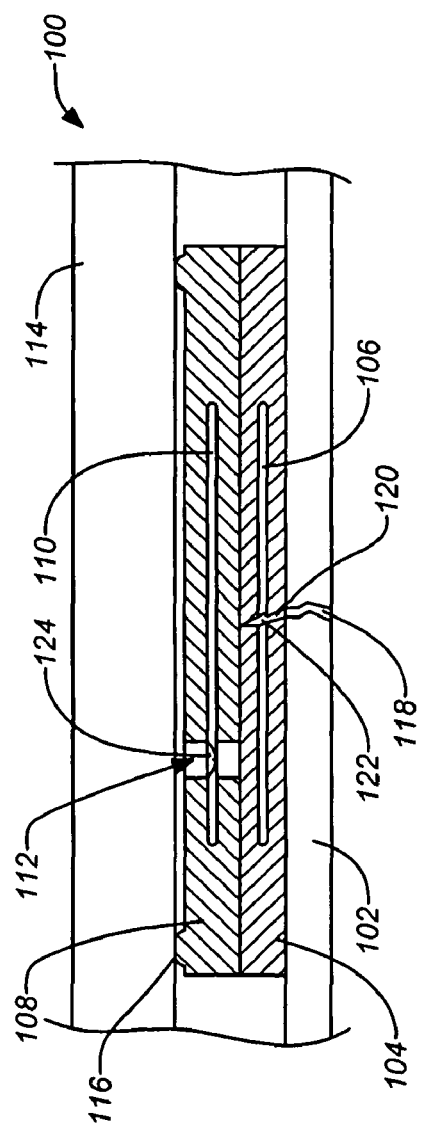

HYBRID RESILIENT AND FRANGIBLE LAYERED STRUCTURAL HEALTH SENSOR

CROSS-REFERENCE TO RELATED APPLICATIONS

This application is related the following co-pending and commonly-assigned U.S. utility patent applications, which are both incorporated by reference herein:

U.S. patent application Ser. No. 11/941,307, by Fay et al. filed Nov. 16, 2007, and entitled "FRACTURE DETECTING STRUCTURAL HEALTH SENSOR"; and U.S. patent application Ser. No. 11/941,367, by Fay et al. filed Nov. 16, 2007, and entitled "CORROSION DETECTING STRUCTURAL HEALTH SENSOR".

BACKGROUND OF THE INVENTION

1. Field of the Disclosure

This disclosure relates to structural testing. Particularly, this disclosure relates to techniques for monitoring the integrity of structural elements over time in service.

2. Description of the Related Art

The need to monitor the integrity of structural elements arises in many different applications. For example, it is necessary to monitor the structures of aircraft. The aircraft stay in service for many years and may experience environments that may exceed design limits resulting in different failure modes, e.g., fatigue, fracture, corrosion. Therefore, it is necessary to regularly check the structural integrity of the vehicle as part of any prudent maintenance program. Similarly, other types of structures may also require regular monitoring. Highway structures such as overpasses and bridges must be regularly checked. Some building structures may also require regular testing. Conventional testing techniques such as visual inspection, x-ray, dye penetrant, and electrical field techniques (e.g., eddy current testing, etc.) for testing structural elements have many drawbacks.

Visual inspection of structural members often requires some degree of disassembly of the structure. This adds greatly to the overall testing cost. For example, visual inspection for aircraft structures requires substantial disassembly of structure and removal of installed equipment in order to provide the access needed to view the areas of interest at a distance adequate to detect corrosion visually.

X-Ray testing, under the broader heading of radiographic testing, requires specialized facilities and government licenses. The technique employs the ability of short wavelength electromagnetic radiation to penetrate various materials. Either an X-ray machine or a radioactive source can be used as a source of photons. Because the amount of radiation emerging from the opposite side of an examined material can be detected and measured, variations in the intensity of radiation are used to determine thickness or composition of material and reveal any defects. Due to safety issues, X-ray testing also typically requires a complete work stoppage on all other tasks while the testing is being performed.

Dye penetrant testing is also time consuming and messy. Dye penetrant inspection is used to reveal surface breaking flaws through the bleedout of a colored or fluorescent dye from the flaw. The technique is based on the ability of a liquid to be drawn into a surface breaking flaw by capillary action. After a period of time, excess surface penetrant is removed and a developer is applied. This acts as a blotter. It draws the penetrant from the flaw to reveal its presence. The consituent penetrant and developer may and their by-products may be identified as hazardous (HAZMAT), requiring costly disposal means.

Finally, inspection methods using the application of electrical fields (e.g., eddy current testing, etc.) are exceptionally time consuming and difficult to read reliably in this type of application and may require alterations to structure. In typical eddy current testing for example, a circular coil carrying an AC current is placed in close proximity to an electrically conductive specimen to be tested. The alternating current in the coil yields a changing magnetic field, which interacts with the test object and induces eddy currents in it. Variations in the phase and magnitude of these eddy currents can be monitored using a second coil, or by measuring changes to the current flowing in the primary coil. The presence of any flaws or variations in the electrical conductivity or magnetic permeability of the test object, will cause a change in eddy current flow and a corresponding change in the phase and amplitude of the measured current. The technique is generally limited to detecting surface breaks or near surface cracking and variations in material composition.

In view of the foregoing, there is a need in the art for apparatuses and methods for efficiently monitoring the integrity of structural elements. In particular, there is a need for such apparatuses and methods to monitor structural elements without requiring time-consuming disassembly. There is also a need for such apparatuses and methods to be light weight and inexpensive to use. There is particularly a need for such apparatuses and methods in aircraft applications. Further, there is a need for such apparasuses and methods to monitor structures for both fractures and possible corrosion and in combination. These and other needs are met by the present disclosure as detailed hereafter.

SUMMARY OF THE DISCLOSURE

A hybrid sensor device for monitoring and testing for both possible fractures and corrosion in structural elements is disclosed. A frangible material layer including a thin breakable conductor sense loop and a resilient material layer including a conductive corrosion sense loop bonded on top of the frangible layer form an assembly which is bonded to a structural element to be tested. Portions of the conductive corrosion sense loop are exposed through weep holes in the resilient material layer. A fracture in the bonded structural element induces a disruption in both the frangible membrane and the thin breakable conductor sense loop and corrosion of the conductive corrosion sense loop changes its electrical properties. Measured electrical property changes of the disrupted conductor sense loop and/or the conductive corrosion sense loop reveal possible damage. Both sensor layers may utilize a single shared wireless communications tag to couple to an electrical measuring device.

A typical sensor embodiment of the invention comprises an apparatus for sensing structural integrity, including a frangible non-conductive material layer, a resilient non-conductive material layer disposed on top of the frangible non-conductive material layer, a breakable conductor sense loop within the frangible non-conductive material layer, and a conductive corrosion sense loop within the resilient non-conductive material layer and having a portion exposed through at least one weep hole in the resilient non-conductive material layer. The frangible non-conductive material is disposed adjacent to a structure surface such that the breakable conductor sense loop can be disrupted by a fracture in the structure surface and the exposed portion of the conductive corrosion sense loop can corrode to induce a change in an electrical property of the conductive corrosion sense loop. In some embodiments, the breakable conductor sense loop and the structure surface may comprise a common material. Typically, the frangible non-conductive material layer is bonded to the structure surface.

Typically, a disruption of the breakable conductor sense loop from the fracture in the structure surface and the change in the electrical property of the conductive corrosion sense loop from may be sensed through an electrical measuring device coupled to both the breakable conductor sense loop and the conductive corrosion sense loop. In further embodiments, the sensor further comprises a wireless communications tag for coupling the electrical measuring device to both the breakable conductor sense loop and the conductive corrosion sense loop. Alternately, a wired connecting device may be used for coupling the electrical measuring device to both the breakable conductor sense loop and the conductive corrosion sense loop.

In further embodiments, a second structure surface may be disposed above the resilient non-conductive material layer, e.g. as used in a gasket configuration. In this case, the resilient non-conductive material layer may comprise one or more sealing ribs against the second structure surface.

In some embodiments, construction of the frangible non-conductive material layer may comprise two layers sandwiching the breakable conductor sense loop. Similarly, construction of the resilient non-conductive material layer may comprise two layers sandwiching the conductive corrosion sense loop.

In a similar manner, a typical method for sensing structural integrity comprises the steps of disposing a frangible non-conductive material having a breakable conductor sense loop within the frangible non-conductive material adjacent to a structure surface, disposing a resilient non-conductive material layer on top of the frangible non-conductive material layer having a conductive corrosion sense loop within the resilient non-conductive material layer and having a portion of the conductive corrosion sense loop exposed through at least one weep hole in the resilient non-conductive material layer, sensing a disruption in the breakable conductor sense loop from a fracture in the structure surface, and sensing a change in an electrical property of the conductive corrosion sense loop from corrosion in the exposed portion of the conductive corrosion sense loop. Method embodiments of the invention may be further modified consistent with the apparatus embodiments described herein.

The features, functions, and advantages that have been discussed can be achieved independently in various embodiments of the present invention or may be combined in yet other embodiments further details of which can be seen with reference to the following description and drawings.

BRIEF DESCRIPTION OF THE DRAWINGS

Referring now to the drawings in which like reference numbers represent corresponding parts throughout:

FIG. 1A illustrates a cross section of an exemplary hybrid resilient and frangible layered structural health sensor;

FIG. 1B illustrates a cross section of an exemplary hybrid resilient and frangible layered structural health sensor indicating a structural failure;

DETAILED DESCRIPTION OF THE PREFERRED EMBODIMENT

1. Overview

Figure 2A:
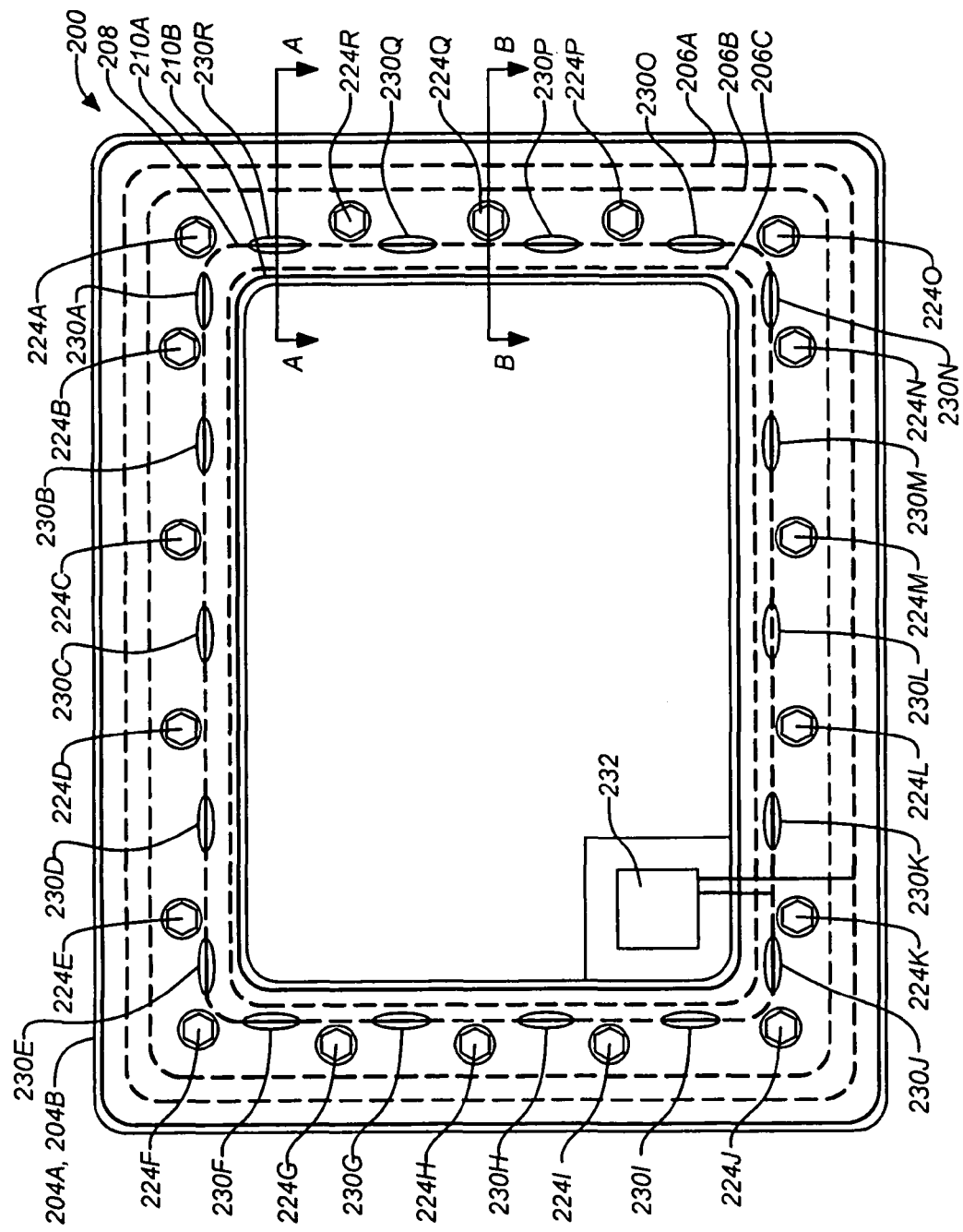
FIG. 2A illustrates a top view of an exemplary hybrid resilient and frangible layered structural health sensor.

As previously mentioned, embodiments of the disclosure are directed to a technique for detecting both a discontinuity caused by a defect (e.g., a fracture) in a structural element as well as possible corrosion in the structural element. This hybrid sensor combines the features of two previously described sensors (a fracture detecting sensor described in U.S. patent application Ser. No. 11/941,307, by Fay et al. filed Nov. 16, 2007, and a corrosion detecting sensor described in U.S. patent application Ser. No. 11/941,367, by Fay et al. filed Nov. 16, 2007) into one integrated sensor with the combined capabilities of both corrosion and crack detection. The dual layer membrane sensor effectively becomes a part of the structure on which it is installed. The sensor can provide the user with corrosion and/or damage status in a quick and reliable way. The sensor does not require special facilities, tools, training or equipment to operate.

The sensor comprises at least two distinct material layers including a frangible non-conductive layer with an embedded breakable conductor sense loop and a resilient non-conductive layer with an embedded conductive corrosion sense loop. This hybrid sensor configuration may be constructed by bonding a resilient gasket corrosion sensor section directly to a frangible fracture sensor section. At installation, the fracture sensor section can be bonded directly to the structure of interest. The frangible non-conductive layer is bonded to a structural element such that a fracture in the structural element produces a corresponding fracture in the membrane and a break in the breakable conductor sense loop. With respect to fracture detection, the structural element may be any material, e.g. metallic or composite. The resilient non-conductive layer is disposed on a top surface of the frangible non-conductive layer and includes at least one weep hole to expose a portion of the conductive corrosion sense loop. Possible corrosion of the nearby structure is indicated by corrosion of the conductive corrosion sense loop which causes a change in its electrical properties.

Disruption of the breakable conductor sense loop and corrosion of the conductive corrosion sense loop are both detectable with an electrical measuring device coupled to the separate loops. Alternately, separate electrical measuring devices may also be used. Connection to the sense loops can be made through an ordinary electrical connector or a wireless communication tag. In the described hybrid sensor, both sensor layers may utilize a single shared wireless communications tag to couple to an electrical measuring device.

In some implementations, a wireless reader measuring device may be used to provide RF signals for energizing circuitry, controlling functionality, and receiving data. The sensor can provide detection capability without the need to remove the installed unit from of service for extended lengths of time, in the absence of corrosion or damage severe enough to require repair. In contrast, conventional techniques for inspecting structures are all exceptionally time consuming and expensive.

Thus, the bonded frangible sensor layer and resilient corrosion sensor layer together can detect hidden fractures, other structural damage and possible corrosion without any component or structural disassembly. In the absence of damage severe enough to require repair, embodiments of the disclosure can mitigate any required disassembly of components or structures as would otherwise be required to perform routine visual inspections. Further, embodiments of the disclosure do not require special facilities, training or government licenses. Embodiments of the disclosure can also provide a quicker process for determining whether structural defects are present without interrupting other work in progress.

A hybrid sensor in accordance with the disclosure can lower the total cost of ownership (e.g., of an aircraft) based on the labor it can save and the additional equipment availability it can provide. Operators will not have to take equipment out of service, provided that there are no incidents of damage that need to be repaired. In contrast, conventional methods require copious labor and extended periods out of service to accomplish—even if no repairs are required. Conventional methods also enhance the risk of maintenance induced damage during the disassembly required for access.

2. Hybrid Layered Fracture and Corrosion Sensor Structure

FIG. 1A illustrates a cross section of an exemplary hybrid resilient and frangible layered structural health sensor 100. The sensor 100 comprises a frangible material layer 104 formed into a thin flat structure that is disposed adjacent to the surface of the structure 102. Typically the frangible material layer 104 is bonded to the structure 102. At least one breakable conductor sense loop 106 is embedded within the frangible material layer 104. The frangible material layer 104 must be non-conductive so as not to short the breakable conductor sense loop 106 which is employed to detect a fracture or other structural failure in the surface of the structure 102.

A separate resilient material layer 108 is disposed on top of the frangible material layer 104. The resilient material layer 108 has at least one conductive corrosion sense loop 110 embedded within it. The resilient material layer 108 includes one or more weep holes 112 which penetrate to expose a portion of the conductive corrosion sense loop 110. The resilient material layer 108 is also non-conductive to avoid shorting the conductive corrosion sense loop 110. Although it is not required, the sensor 100 may be employed in a gasket configuration. In this case, the surface of a second structure 114 is disposed above the resilient non-conductive material layer 108. In this configuration, the resilient non-conductive material layer 108 may include one or more sealing ribs 116 against the surface of the second structure 114.

FIG. 1B illustrates a cross section of an exemplary hybrid resilient and frangible layered structural health sensor indicating a structural failure. A fracture 118 appearing in the surface of the structure 102 induces a break 120 in the frangible material layer 104 which in turn carries through to cause a break 122 in the breakable conductor sense loop 104. Possible corrosion in the nearby structures 102, 114 (or other structure not shown) is detected by the resilient non-conductive material layer 108 of the sensor 100. Typically, the detected disruption in the breakable conductor sense loop 104 is a break (which may be a complete break or a partial break through the breakable conductor sense loop 104). However, any variation in the measured electrical properties of the breakable conductor sense loop 104, (e.g., an increase in resistance) may also be employed to detect the disruption and indicate a fracture or other problem in the underlying structure.

Possible corrosion in the nearby structures 102, 114 (or other structure not shown) is indicated by corrosion of the conductive corrosion sense loop 110 in portion exposed by the one or more weep holes 112. Any corrosion 124 that develops on the conductive corrosion sense loop 110 in the one or more weep holes 112 in the resilient non-conductive material layer 108 will affect the electrical properties of the conductive corrosion sense loop 110. The material of the conductive corrosion sense loop 110 may be selected to be susceptible to corrosion so that any moisture that comes in contact with the area will enter the weep hole 112 and cause at least a partial reduction of the exposed portion of the conductive corrosion sense loop 110. This will result in an increase in the effective resistance of the conductor as the cross sectional area of the conductor is reduced by the corrosion. Thus, although actual corrosion of the structures 102, 114 may not yet exist, the weep hole 112 allows the conductive corrosion sense loop 110 to provide an early warning of possible corrosion to the structural elements due to the presence of moisture. Excessive corrosion that may develop in the weep holes 112 in the resilient material layer 108 may also cause a disruption in the conductive corrosion sense loop 110 as well. It should be noted that design of the conductive corrosion sense loop 110 may be optimized such that the portions of the conductive corrosion sense loop 110 may be treated differently or comprise a different material than the unexposed portions of the conductive corrosion sense loop 110 to enhance the corrosion sensitivity in this area.

Ends of both the breakable conductor sense loop 106 and the conductive corrosion sense loop 110 are connected to a connecting device which is coupled to a measuring device that detects the fracture or corrosion as illustrated in example hybrid layered fracture and corrosion sensor installation described in the next section.

In one example, the frangible material layer may be constructed from two layers of thin plastic frangible film which contains the one or more fine wire sense loops sandwiched between. The frangible frangible material layer may be curable such that it is flexible prior to installation, but becomes rigid and brittle when fully cured. As previously described, when damage, such as a crack occurs on the underlying structure, the frangible membrane cracks as well, breaking the wire sense loop at the location of the damage. The frangible material layer is a non-conductive material that may be self-adhesive at installation and effectively seals and protects the underlying structure from corrosion.

Similarly, the resilient material layer may also be constructed from two layers of thin plastic which contains one or more wire sense loops. The resilient material layer may also be curable, but it cures to a resilient material. The resilient material layer is also non-conductive and may be self-adhesive to the top of the frangible material layer. As described above, one or more weep holes in the top of the resilient material layer permit the conductive corrosion sense loop to indicate possible corrosion.

The sensor may be installed at structural locations where cracks and/or corrosion are a concern, such as fastener holes and cutouts in pressurized structure. At appropriate intervals, an operator uses a reader device to energize and read the sensor. Either a wireless reader device or another external device may be used to compare the readings of a sense loop to those of a reference value measured at each specific installation to determine if possible corrosion or damage is present. The reference value can be determined when the sensor is designed for a specific application and manufactured. The reference value for the specific application can either exist in written form for manual measurement and analysis or be loaded into the wireless reader for automatic analysis.

The frangible and resilient layer share some common properties but also have distinct characteristics. In general, the frangible material layer is non-porous and frangible (brittle) after installation. Materials for the frangible material layer may have characteristics similar to paint coatings in appearance. The objective is that the composition of the frangible material layer should match the structure material it is bonded to such that if a crack occurs in the structural element, the frangible material layer cracks as well, breaking the conductor which forms the sense loop. On the other hand, the resilient material layer should be flexible after installation. Both material layers may be either a pre-formed device or fabricated on site. Both the frangible and resilient material layers should be an effective electrical insulator and flexible enough prior to installation to permit ease of installation. Both material layers should have good shelf-life quality to permit stocking of spares. Both layers must be non-corrosive, particularly to the conductive corrosion sense loop. The proper layer and sense loop materials and sizes and electrical measurement characteristics can be selected for a specific installation to maximize sensor performance. The different materials for the frangible membrane layer may comprise, but are not limited to, polycarbonate, urethane, polyurethane, enamel, polyester, acrylic, epoxy, and a wide variety of plastics and other similar materials. The materials for the resilient gasket layer may comprise, but are not limited to, silicone, rubber, nitrile, Buna-N, neoprene, Teflon, and other similar materials.

The sense loops may be custom tailored to the specific application. For the breakable conductor sense loop it can typically be constructed from the same material (e.g., base metal and alloy) as the structural element at the installed interface. The configuration and size of the sense loop should be appropriate to ensure the conductor breaks when and if the membrane breaks. The conductive corrosion sense loop need not be breakable. Materials for the sense loop include, but are not limited to aluminum, steel, copper, magnesium, titanium, and other similar materials. A membrane sensor device may also be implemented in a gasket configuration as described in the next section.

3. Example Hybrid Layered Fracture and Corrosion Sensor Installation

Figure 2B:
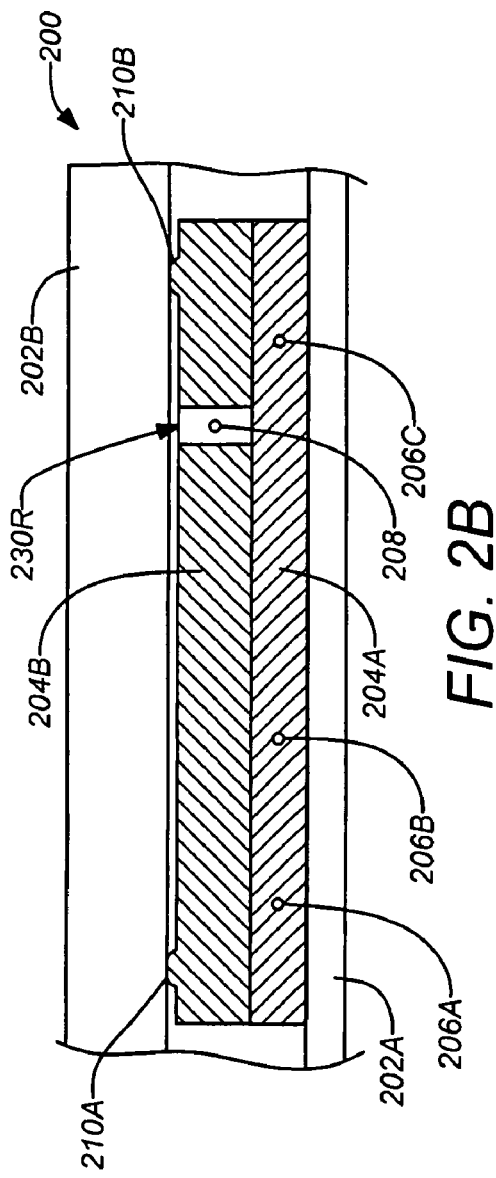
FIG. 2B illustrates cross section A-A of the exemplary hybrid resilient and frangible layered structural health sensor.
Figure 2C:
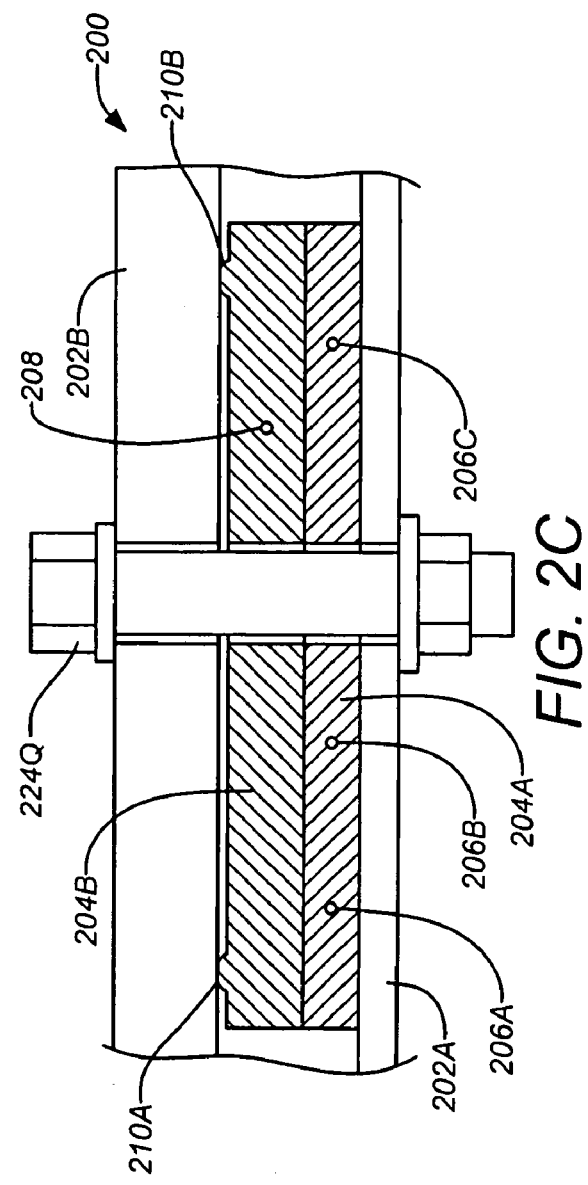
FIG. 2C illustrates cross section B-B of the exemplary hybrid resilient and frangible layered structural health sensor.

FIGS. 2A to 2C illustrate a top view and two cross sections, respectively of an exemplary hybrid resilient and frangible layered structural health sensor 200. FIG. 2B illustrates cross section A-A and FIG. 2C illustrates cross section B-B of the exemplary hybrid resilient and frangible layered structural health sensor 200 shown in FIG. 2A. The sensor 200 comprises a frangible and a resilient material layer 204A, 204B formed into a thin flat structure that is disposed adjacent between the surfaces of two structures 202A, 202B as shown in the cross sections of FIGS. 2B and 2C. In this case, the frangible material layer 204A is disposed on the surface of a first structure 202A. In this example, three breakable conductor sense loops 206A, 206B, 206C are embedded within the frangible material layer 204A. Here also, the frangible material layer 204A must be non-conductive so as not to short the breakable conductor sense loops 206A, 206B, 206C employed to detect a fracture or other structural failure in the surface either of the structures 202A, 202B in the manner previously described regarding FIGS. 1A and 1B.

The resilient material layer 204B is disposed on top of the frangible material layer 204A. The resilient material layer 204B includes multiple weep holes 230A-230R which penetrate the layer 204B to expose distinct portions of a conductive corrosion sense loop 208. Thus, the conductive corrosion sense loop 208 can be used to provide early detection of corrosion as previously described regarding FIGS. 1A and 1B. The gasket configuration of the sensor 200 can also include one or more ribs 210A, 210B built into the top surface of the resilient material layer 204B. The ribs 210A, 210B are designed to provide a seal against the adjacent surface of the structure 202B.

As previously described, the conductive corrosion sense loop 208 material may be selected to be susceptible to corrosion so that any moisture that comes in contact with the area will enter one or more of the weep holes 230A-230R and cause at least a partial erosion of the conductor. This will result in an increase in the effective resistance of the conductor as the cross sectional area of the conductor is reduced by the corrosion. Thus, although actual corrosion of the structures 202A, 202B may not exist yet, the weep holes 230A-230R allow the conductive corrosion sense loop 208 to provide an early warning of possible corrosion to the structural element due to the presence of moisture. It should be noted that the gasket configuration is particularly well suited for early corrosion detection because the top surface of resilient material layer 204B is intended to remain sealed from the environment (with or without the sealing ribs 210A, 210B). Thus, a visual inspection of the area would not reveal any moisture present in the weep holes 230A-230R.

Referring to FIG. 2A, the ends of both the conductive corrosion sense loop 208 and the three breakable conductor sense loops 206A, 206B, 206C are connected to a connecting device which can then be coupled to a measuring circuit that detects the fracture or corrosion. Communication with the sensor 200 may be accomplished using any known technique. In this configuration, the two layers 204A, 204B are sandwiched between the surfaces of two structures 202A, 202B as described in FIGS. 2B and 2C. For example, the structures 202A, 202B may be a joint between two components in an aircraft. A series of bolts 224A-224R are disposed around the interface between the structures 202A, 202B. The breakable conductor sense loops 206A, 206B, 206C are embedded within the frangible material layer 204A as previously described and is routed around the interface as well. The breakable conductor sense loops 206A, 206B, 206C are laid perpendicular to where any structural failures are likely to appear.

In addition, there are also weep holes 230A-230R at various locations along the conductive corrosion sense loop 208 which operate as previously described to provide an early warning of corrosion. Ribs 210A, 210B are also laid out around the perimeter of both the inner and outer edges of the sensor 200 on the top side of the resilient material layer 204B as previously described in FIGS. 2B and 2C to seal the layer surface and the structure 202B surface from moisture.

The breakable conductor sense loops 206A, 206B, 206C and the conductive corrosion sense loop 208 of the gasket sensor 200 are coupled to a connecting device 232 which is used to connect to a electrical measuring device that measures changes in the electrical properties of the loops 206A, 206B, 206C, 208 (e.g., resistance increase indicating corrosion or an open circuit indicating a fracture). The electrical measuring device can be any known device capable of measuring the appropriate electrical properties of the loops 206A, 206B, 206C, 208. In a simple implementation, the connecting device 232 may comprise an electrical connector. However, the connecting device 232 may also comprise a wireless communication tag as described in the next section which affords many advantages beyond a simple electrical connector. The wireless communication tag incorporates some of the reader device with the tag.

4. Wireless Communication with Sensor

Figure 3A:
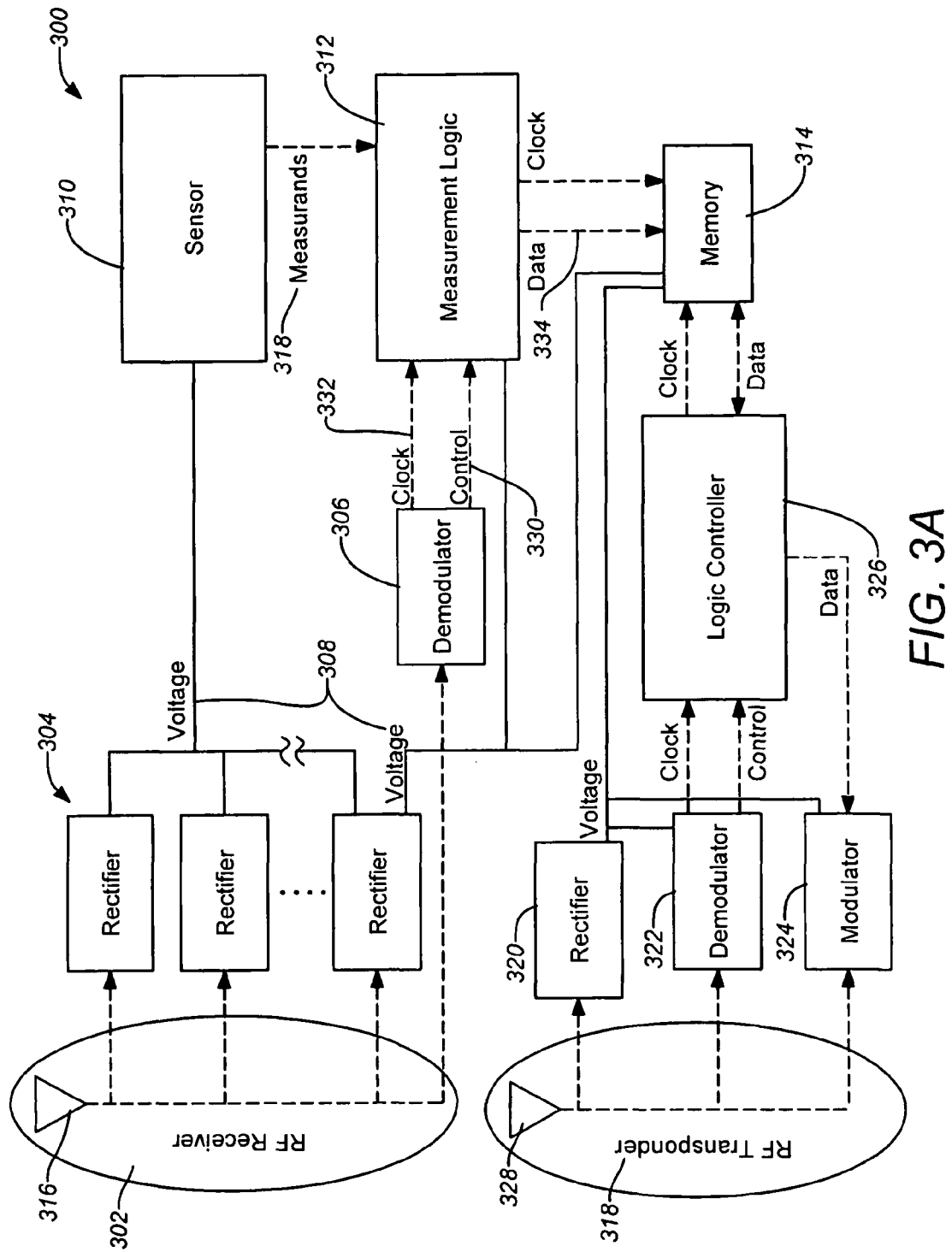
FIG. 3A illustrates a wireless communication tag that may be coupled to a structural sensor.

FIG. 3A illustrates a wireless communication tag 300 that may be coupled to a structural sensor 310. The example wireless communications tag 300 comprises one or more RF receivers 302. The one or more receivers 302 are coupled to a series of rectifier circuits 304 and a demodulator 306. The RF receivers should be designed with one or more resonant frequencies to maximize the excitation of the receiver rectifier circuits and demodulators. Each RF receiver rectifier circuit 304 may be associated with a specific series and/or parallel resonant frequency to maximize signal voltage 308 generated to power necessary sections of the tag and sensor 310 (i.e., the sense loop) during different modes of operation. Voltage 308 from the rectifiers 304 is supplied to the sensor 310 that yields measurands 318 to the measurement logic circuit 312. The clock 302 and control 330 signals from the demodulator 306 are used to control the measurement logic 312 to convert measurands 318 into data 334 transferred to memory 314. The demodulator 306 clock 332 is used to generate the clock signal from the measurement logic 312 for clocking data into memory 314. The clock and control signals from the demodulator 322 are used to control the logic controller 326 to read and write data into memory 314.

The RF receiver 302 may comprise one or more series and/or parallel resonant frequencies for the receiver demodulator 306 to properly control and synchronize the measurement logic 312 and targeted locations of the memory 314. The RF receiver 302 antenna 316 may support a series and parallel resonant frequencies by using a distributed capacitance, inductance, and resistance as known in the art. The RF receiver 302 may be designed to operate using OFDM, CDMA or any other multi-carrier resonant frequencies across the frequency spectrum known in the art. The RF receiver 302 should be designed with safeguard features to ensure inappropriate operations do not occur based on safety requirements.

Figure 3B:
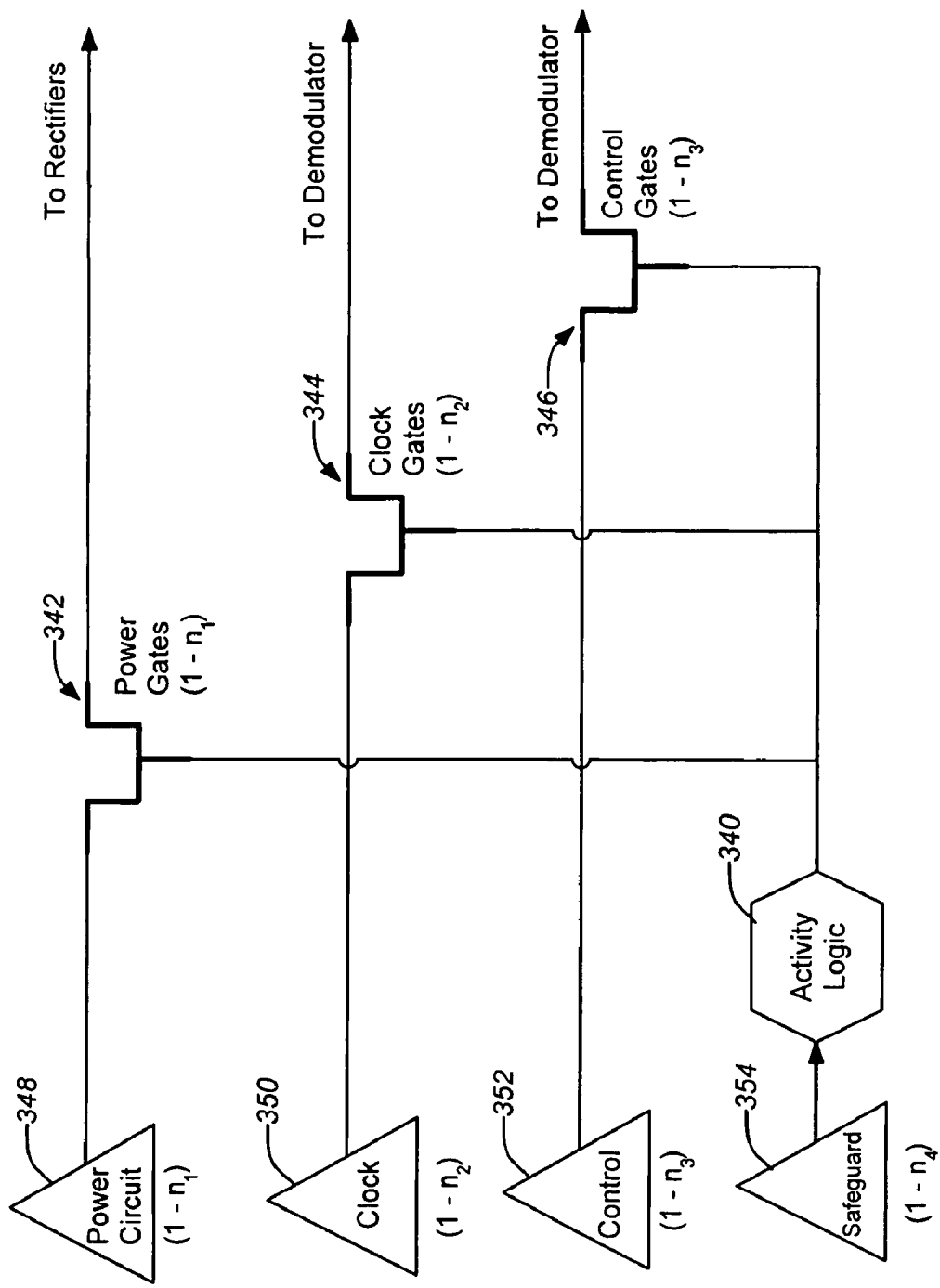
FIG. 3B illustrates an example safeguard feature for an receiver in a wireless communication tag.

FIG. 3B illustrates an example safeguard feature for a receiver 302 (such as the RF receiver 302 of FIG. 3A) in a wireless communication tag 300. Sets of unique resonant frequency (or frequency pattern) inputs 348 ($1-n_1$), 350 ($1-n_2$), 352 ($1-n_3$) are used to respectively direct the power, clock and control of the device. Typically, the sets of power resonant frequency inputs 348 direct the rectifiers (e.g., rectifiers 304 of FIG. 3A), while the the sets of clock and control resonant frequency inputs 350, 352 direct the demodulator (e.g., demodulator 306 of FIG. 3A) of the device. Embodiments of the disclosure may further implement a safeguard feature for preventing inadvertent activities of the overall device may use a set of safeguard resonant frequency inputs 354 ($1-n_4$) per device. (The safeguard resonant frequency inputs 354 may be either unique resonant frequency patterns or a subset of the frequencies used from the power, clock, and/or control resonant frequencies inputs 348, 350, 352.) The activity logic 340 operates to enable the power, clock and control gates 342, 344, 346, respectively, only when the set of safeguard resonant frequency inputs 354 (e.g., specific frequencies with corresponding amplitudes) meet the required safeguard conditions of the activity logic circuit 340. For example, the activity logic 340 may require specific timing or sequencing of the receiving sets of frequency inputs 348, 350, 352, 354. The safeguard conditions may be statically part of the activity logic circuit 340 or implemented in a way that allows for reconfiguration, e.g., through a programmable element.

Those skilled in the art will appreciate that a similar safeguard architecture can be readily applied for an transponder (such as the RF transponder 318 of FIG. 3A). The RF transponder 318 should be designed with one or more resonant frequencies to maximize the excitation of the one or more transponder rectifier circuits 320, demodulators 322, and modulators 324. The RF transponder 318 may operate using RFID technology known in the art. Each RF transponder rectifier circuit 320 should be associated with a specific series and/or parallel resonant frequency to maximize signal voltage generated to power necessary sections of the tag during different modes of operation. The RF transponder 318 may be designed with one or more series and/or parallel resonant frequencies for the transponder demodulator 322 to properly control and sync the transponder control logic 326 and targeted locations of the memory 314. The RF Transponder 318 should be designed with one or more series and/or parallel resonant frequencies for the transponder modulator 324 to properly generate transmission signals externally to a reader (not shown) through the antenna 328. The RF transponder 318 should include all or a subset of the frequency bands supporting RFID as known in the art. The RF Transponder should be designed with safeguard features to ensure inappropriate operations do not occur based on safety requirements.

Referring back to FIG. 3A, the measurement logic 312 may support the input measurands 318 from the sensor 310 (sense loop), convert the measurand 318 values into a digital format, and write the values into targeted portions of the memory 314 on a data channel 334. The measurement logic 312 may support serial or parallel control 330 and clock 332 signals. The memory 314 may support, at minimum, non-volatile reference information (e.g., identification, encryption key) and non-volatile or volatile value fields (e.g., measurements). Further, the memory 314 may also support serial or parallel reads and writes. All demodulators 306, 322 may provide serial and/or parallel control and clock signals. The logic controller 326 may provide read capabilities of the targeted memory 314 region and simultaneously input into the modulator 324.

It is important to note that the wireless communication tag may be designed to operate with a range sensors such as that previously described including both fracture and/or corrosion sensing. Additionally, the wireless communication tag may be designed to operate with any other sensor that may be installed to monitor a structure.

In one example, multiple structural sensors (e.g., hybrid fracture and corrosion sensors) each have a wireless communication tag are installed in an aircraft structure and employed under an overall testing plan. The sensors are first installed at their various location during the aircraft build. A first reading is performed for all the sensors to validate their functioning and to provide identification and sensor results with a reader device. Following this, the aircraft build is completed and the sensors are then revalidated for functionality. (This sensor installation may occur during the original aircraft build or a retrofit during aircraft maintenance.) The identification and location of the various sensors are recorded. The sensors are next read at a scheduled inspection and any indicated problems repaired. An example reading process is described hereafter.

A wireless reader device is employed to read identification numbers of sensors by transmitting a "ping" to a localized area of the aircraft structure where one or more sensors are installed. Any sensors in the area respond with their identification numbers. The indentification numbers are then cross-referenced to aircraft records to determine the sensor locations. The reader then interrogates all the sensors by transmitting another "ping" to energize sense element circuitry of the sensors. Each sensor tag is powered by the voltage induced in it by the readers transmitted power. The wireless communication tag then verifies that the induced power is within system specifications. An error message is returned to the reader if this fails. If successful, the sense portion of the tag then energizes the conductor sense loop. The sense portion of the tag then reads electrical characteristics of the energized sense loop. The tag then transmits sense element readings to the reader for analysis. The reader then receives the transmitted tag data and compares the values to reference standards for the respective sensors. Finally, the reader displays the inspection results for each sensor. The next regular inspection is scheduled if the result is successful or a repair is scheduled if a failure is indicated.

5. Method of Monitoring Structural Integrity

Figure 4:
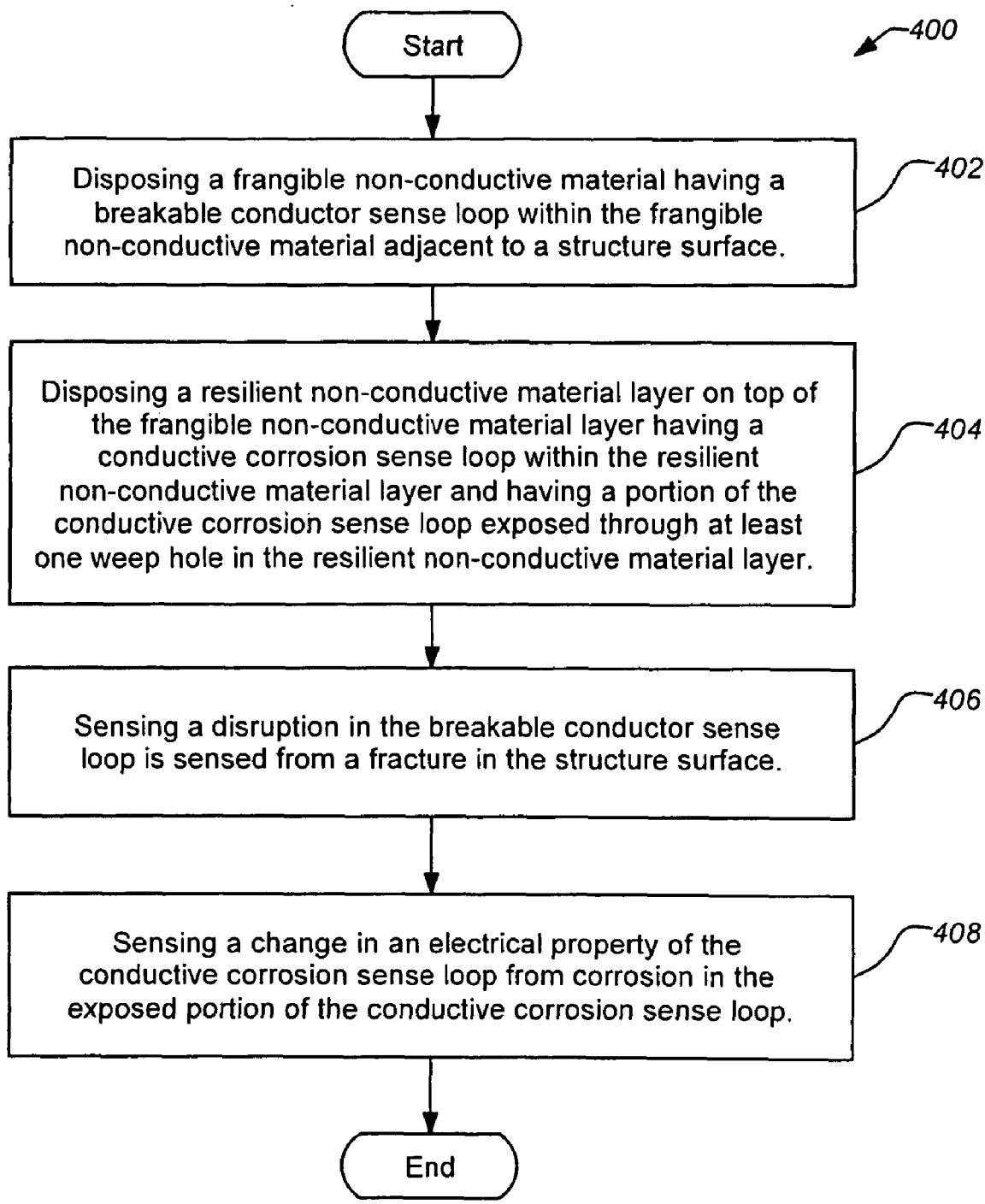
FIG. 4 is a flowchart of a method of sensing a structural integrity.

FIG. 4 is a flowchart of a method 400 of sensing a structural integrity. The method 400 begins with a first operation 402 of disposing a frangible non-conductive material having a breakable conductor sense loop within the frangible non-conductive material adjacent to a structure surface. In operation 404, a resilient non-conductive material layer is disposed on top of the frangible non-conductive material layer having a conductive corrosion sense loop within the resilient non-conductive material layer and having a portion of the conductive corrosion sense loop exposed through at least one weep hole in the resilient non-conductive material layer. In operation 406, a disruption in the breakable conductor sense loop is sensed from a fracture in the structure surface. In operation 408, a change in an electrical property of the conductive corrosion sense loop from corrosion in the exposed portion of the conductive corrosion sense loop is sensed. This method 400 for sensing structural integrity may be modified consistent with any of the devices or other methods described herein.

It should be noted that typically operation 404 is performed first in a manufacturing process bonding the resilient non-conductive material layer to the frangible non-conductive material layer to produce the hybrid sensor and operation 402 is performed later when the hybrid sensor is installed on the structure. However, these two operations may be performed in the opposite order. For example, the hybrid sensor may be assembled as it is installed on the structure with the frangible non-conductive material layer first bonded to the structure in operation 402 and the resilient non-conductive material layer bonded on top of the frangible non-conductive material layer thereafter in operation 404.

Figure 5:
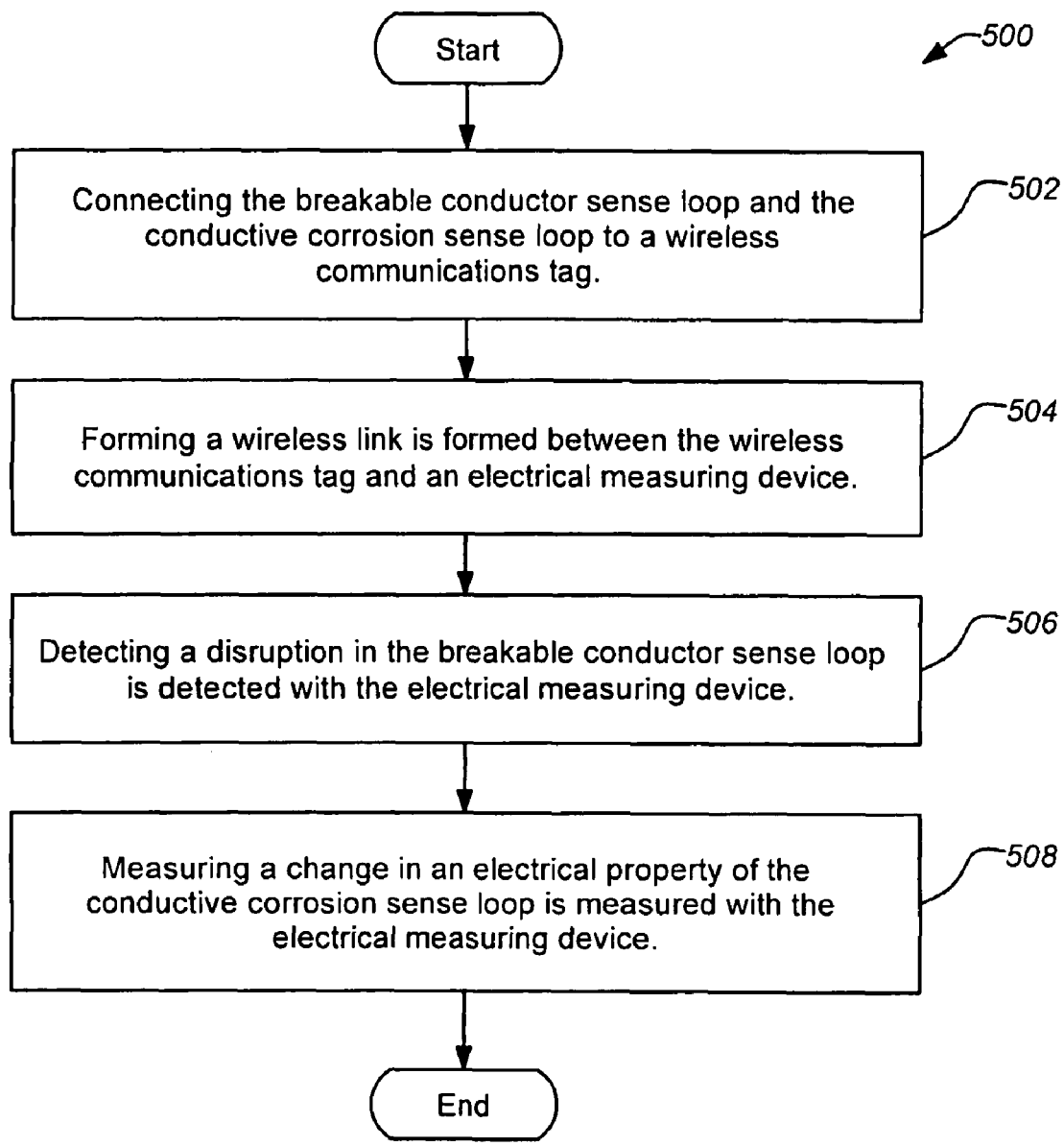
FIG. 5 is a flowchart of a sub-method of sensing using the sense loops for the the method of sensing structural integrity of FIG. 4.

FIG. 5 is flowchart of a sub-method 500 of operations 406 and 408 for sensing using the sense loops. Sub-method 500 of sensing with the sense loops begins with the operation 502 of connecting the breakable conductor sense loop and the conductive corrosion sense loop to a wireless communications tag. In operation 504 a wireless link is formed between the wireless communications tag and an electrical measuring device. In operation 506, a disruption in the breakable conductor sense loop is detected with the electrical measuring device. In operation 508, a change in an electrical property (e.g., a resistance change) of the conductive corrosion sense loop is measured with the electrical measuring device. This method 500 for sensing with the two sense loops may be modified consistent with any of the devices or other methods described herein.

This concludes the description of various embodiments of the present invention. The foregoing description including the described embodiment of the disclosure has been presented for the purposes of illustration and description. It is not intended to be exhaustive or to limit embodiments of the invention to the precise forms disclosed. Many modifications and variations are possible within the scope of the foregoing teachings. Additional variations of the present disclosure may be devised without departing from the inventive concept as set forth in the following claims.

What is claimed is:

1. An apparatus for sensing structural integrity, comprising:
   a frangible non-conductive material layer;
   a resilient non-conductive material layer disposed on top of the frangible non-conductive material layer;
   a breakable conductor sense loop within the frangible non-conductive material layer; and
   a conductive corrosion sense loop within the resilient non-conductive material layer and having a portion exposed through at least one weep hole in the resilient non-conductive material layer;
   wherein the frangible non-conductive material is disposed adjacent to a structure surface such that the breakable conductor sense loop is disrupted when a fracture occurs in the structure surface and the exposed portion of the conductive corrosion sense loop corrodes when moisture enters the at least one weep hole to induce a change in an electrical property of the conductive corrosion sense loop and wherein the non-conductive material layers are disposed between the structure surface and a second structure surface in a gasket configuration such that both surfaces of the non-conductive material layers are sealed from moisture.

2. The apparatus of claim 1, wherein a disruption of the breakable conductor sense loop from the fracture in the structure surface and the change in the electrical property of the conductive corrosion sense loop from is sensed through an electrical measuring device coupled to both the breakable conductor sense loop and the conductive corrosion sense loop.

3. The apparatus of claim 2, further comprising a wireless communications tag for coupling the electrical measuring device to both the breakable conductor sense loop and the conductive corrosion sense loop.

4. The apparatus of claim 2, further comprising a wired connecting device for coupling the electrical measuring device to both the breakable conductor sense loop and the conductive corrosion sense loop.

5. The apparatus of claim 1, wherein the breakable conductor sense loop and the structure surface comprise a common material.

6. The apparatus of claim 1, wherein the frangible non-conductive material layer is bonded to the structure surface.

7. The apparatus of claim 1, wherein the resilient non-conductive material layer comprises one or more sealing ribs against the second structure surface.

8. The apparatus of claim 1, wherein the frangible non-conductive material layer comprises two layers sandwiching the breakable conductor sense loop.

9. The apparatus of claim 1, wherein the resilient non-conductive material layer comprises two layers sandwiching the conductive corrosion sense loop.

10. The apparatus of claim 1, wherein at least one of the resilient non-conductive material layer and the frangible non-conductive material layer is self-adhesive.

11. A method for sensing structural integrity, comprising the steps of
   disposing a frangible non-conductive material having a breakable conductor sense loop within the frangible non-conductive material adjacent to a structure surface;

disposing a resilient non-conductive material layer on top of the frangible non-conductive material layer having a conductive corrosion sense loop within the resilient non-conductive material layer and having a portion of the conductive corrosion sense loop exposed through at least one weep hole in the resilient non-conductive material layer;

sensing a disruption in the breakable conductor sense loop from a fracture in the structure surface; and sensing a change in an electrical property of the conductive corrosion sense loop from corrosion in the exposed portion of the conductive corrosion sense loop;

wherein the non-conductive material layers are disposed between the structure surface and a second structure surface in a gasket configuration such that both surfaces of the non-conductive material layers are sealed from moisture.

12. The method of claim 11, wherein a disruption of the breakable conductor sense loop from the fracture in the structure surface and the change in the electrical property of the conductive corrosion sense loop from is sensed through an electrical measuring device coupled to both the breakable conductor sense loop and the conductive corrosion sense loop.

13. The method of claim 12, wherein a wireless communications tag couples the electrical measuring device to both the breakable conductor sense loop and the conductive corrosion sense loop.

14. The method of claim 12, wherein a wired connecting device couples the electrical measuring device to both the breakable conductor sense loop and the conductive corrosion sense loop.

15. The method of claim 11, wherein the breakable conductor sense loop and the structure surface comprise a common material.

16. The method of claim 11, wherein the frangible non-conductive material layer is bonded to the structure surface.

17. The method of claim 11, wherein the resilient non-conductive material layer comprises one or more sealing ribs against the second structure surface.

18. The method of claim 11, wherein the frangible non-conductive material layer comprises two layers sandwiching the breakable conductor sense loop.

19. The method of claim 11, wherein the resilient non-conductive material layer comprises two layers sandwiching the conductive corrosion sense loop.

20. The method of claim 11, wherein at least one of the resilient non-conductive material layer and the frangible non-conductive material layer is self-adhesive.

* * * * *